US00PP25041P2

(12) United States Plant Patent
Tellwright

(10) Patent No.: US PP25,041 P2
(45) Date of Patent: Nov. 4, 2014

(54) ***NEMESIA* PLANT NAMED 'FLEURFRAM'**

(50) Latin Name: *Nemesia foetens*
Varietal Denomination: FLEURFRAM

(71) Applicant: Planthaven International, Inc., Santa Barbara, CA (US)

(72) Inventor: Martine Tellwright, Barnham (GB)

(73) Assignee: Martine Tellwright (GB)

( * ) Notice: Subject to any disclaimer, the term of this patent is extended or adjusted under 35 U.S.C. 154(b) by 75 days.

(21) Appl. No.: 13/694,632

(22) Filed: Dec. 20, 2012

Related U.S. Application Data

(60) Provisional application No. 61/632,231, filed on Jan. 20, 2012.

(51) Int. Cl.
*A01H 5/00* (2006.01)

(52) U.S. Cl.
USPC ..... Plt./458

(58) Field of Classification Search
USPC ..... Plt./458
See application file for complete search history.

*Primary Examiner* — Kent L Bell
(74) *Attorney, Agent, or Firm* — Bethany Reid Roahrig; Cochran Freund & Young LLC

(57) ABSTRACT

A new cultivar of *Nemesia* named 'FLEURFRAM' that is characterized by compact upright habit, small fresh green foliage and a prolific display of large raspberry red flowers when first open becoming lilac blue in color as they age and fade. The flowers also exhibit a maroon-colored palate or "eye". In combination these traits set 'FLEURFRAM' apart from all other existing varieties of *Nemesia* known to the inventor.

2 Drawing Sheets

Genus: *Nemesia*.
Species: *foetens*.
Denomination: 'FLEURFRAM'.

BACKGROUND OF THE INVENTION

The present invention relates to a new and distinct cultivar of *Nemesia* plant grown as an ornamental for use in garden and landscape borders, or in containers. The new variety is known botanically as *Nemesia foetens* and will be referred to hereinafter by the cultivar name 'FLEURFRAM'.

'FLEURFRAM' resulted from a formal breeding program begun by the inventor in 1998 at her nursery in West Sussex, United Kingdom. The purpose of the breeding program is to produce new varieties of *Nemesia* that exhibit compact habit and new flower colors and color combinations.

In 2008, the inventor conducted controlled cross-pollination between two unreleased and unpatented selections of *Nemesia* from the inventor's breeding program, namely *Nemesia* code number 825 (unpatented) as male parent and *Nemesia* code number 832 (unpatented) as female parent. 'FLEURFRAM' was selected by the inventor in 2009 for its attractive multicolored inflorescence which is comprised of individual flowers of varying age and color.

'FLEURFRAM' is distinguishable from the male parent, '825' as follows:

Whereas the flowers of 'FLEURFRAM' are raspberry red, fading to lilac-blue, with a maroon palate or "eye", the flowers of the male parent are red and do not exhibit any fading with age. Additionally 'FLEURFRAM' exhibits an upright habit with a smaller leaf, '825' has a trailing habit and produces a larger size leaf.

'FLEURFRAM' is distinguishable from the female parent, '832' as follows:

Whereas the habit of 'FLEURFRAM' is compact with a shorter overall plant size at maturity, '832' exhibits an open habit with a taller overall plant size at maturity.

The closest comparison plant known to the inventor is the inventor's variety, 'FLEURIPI' (U.S. Plant Pat. No. 16,851). 'FLEURIPI' is distinguishable from 'FLEURFRAM' as follows: Mature plants of 'FLEURIPI' are shorter in height than plants of 'FLEURFRAM'. 'FLEURIPI' has smaller strong pink colored flowers compared to 'FLEURFRAM' which are larger in size and which vary from raspberry red fading to lilac-blue with a maroon palate or "eye" in color.

'FLEURFRAM' was first asexually propagated by the inventor in 2009 in an unheated greenhouse at the inventor's nursery in West Sussex, United Kingdom using softwood cuttings. The inventor has determined that 'FLEURFRAM' is stable and uniform, and reproduces true to type in successive generations of asexual reproduction.

The first public distribution anywhere in the world of any plants of 'FLEURFRAM' took place in April 2011 when the inventor commenced deliveries of plants to garden centers in the United Kingdom. These plants had all been grown by the inventor from plants which the inventor had privately commissioned to be produced solely for the inventor under virus-free conditions. The inventor filed an application for European Community Plant Breeders' Rights for 'FLEURFRAM' on Dec. 22, 2011, Serial Number 2011/3170. That application states a first date of sale in Europe as 10 Jan. 2011 and refers to the purchase by the inventor of the privately-commissioned plants above.

SUMMARY OF THE INVENTION

The following traits have been repeatedly observed and represent the distinguishing characteristics of 'FLEURFRAM'. In combination these traits set the new cultivar apart from all other existing varieties of Nemesia known to the inventor. 'FLEURFRAM' has not been tested under all possible conditions and phenotypic differences may be observed with variations in environmental, climatic, and cultural conditions, without however, any variance in genotype.

1. 'FLEURFRAM' exhibits a compact upright habit.
2. A 6 months old plant of 'FLEURFRAM' grown in a 9 cm. container is 15 cm. in height and 10-12 cm. in width.
2. A 9 months old plant of 'FLEURFRAM' grown in a 13 cm container is 25-30 cm. in height and 25-30 cm. in width.
3. 'FLEURFRAM' exhibits large flowers which are raspberry red in color when first open becoming lilac-blue in color as they age and fade.
4. The flowers of 'FLEURFRAM' exhibit a maroon-colored palate or "eye".
5. 'FLEURFRAM' has a long blooming period, from early spring until fall.
6. 'FLEURFRAM' is hardy to −6° Celsius and survives in USDA Zone 9.

BRIEF DESCRIPTION OF THE DRAWINGS

The accompanying color drawings illustrate the overall appearance of the new *Nemesia* cultivar named 'FLEURFRAM' showing the colors as true as it is reasonably possible to obtain in colored reproductions of this type.

The drawing labeled

The drawing labeled

Figure 1:
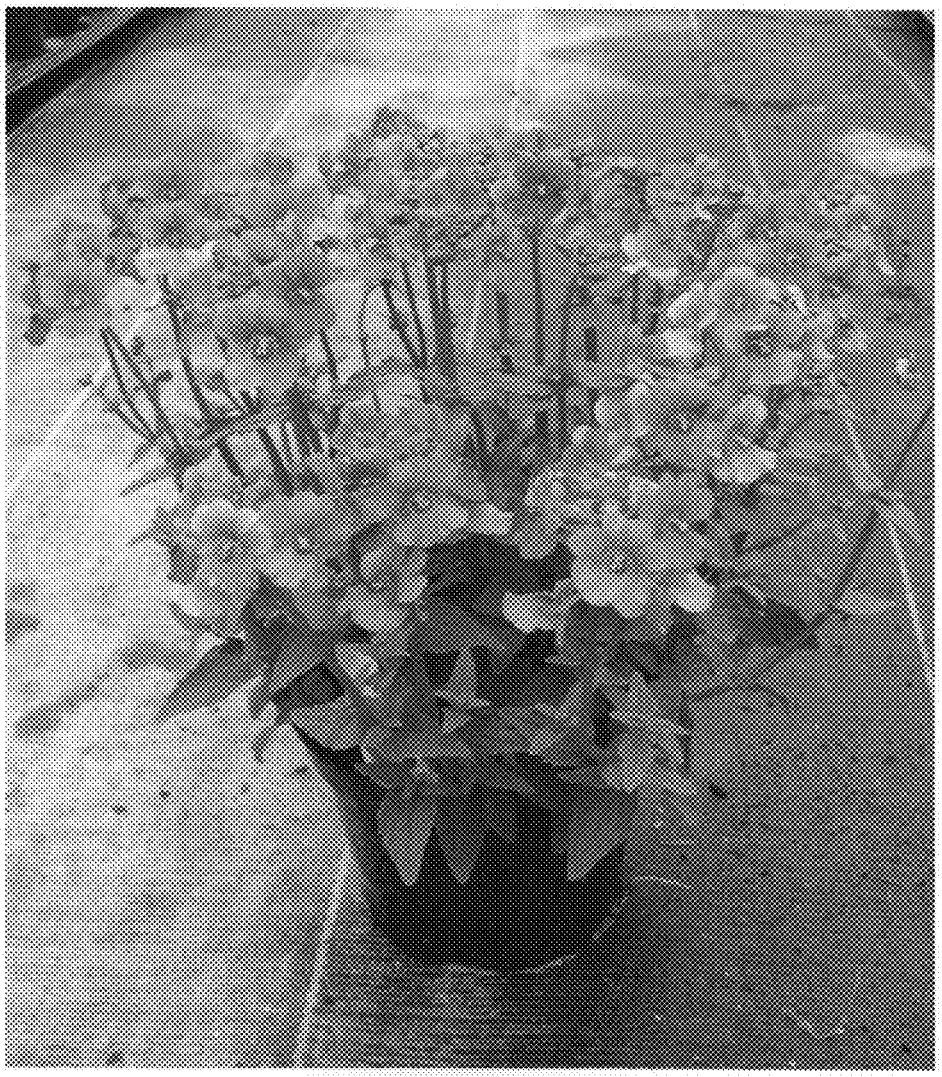
FIG. 1 shows an 8 month old plant of 'FLEURFRAM' grown from a cutting. The plant has been grown in a 1-litre container in a frost-free greenhouse in West Sussex, United Kingdom. The plant has been grown naturally, without the use of pinching or chemical growth regulator treatments.
Figure 2:
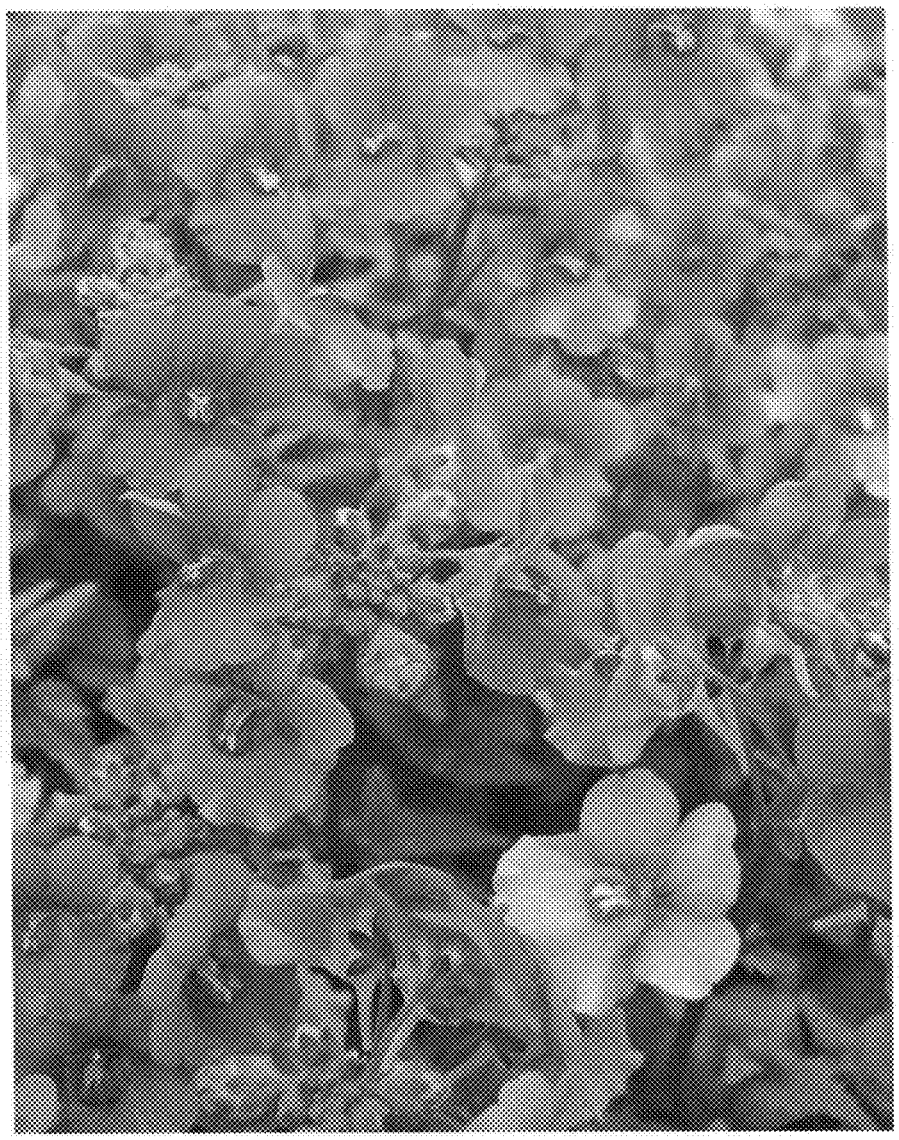
FIG. 2 depicts a close-up view of the flowers of 'FLEURFRAM'.

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Nemesia* cultivar named 'FLEURFRAM'. Observations, measurements, values and comparisons were collected in Santa Barbara, Calif. from a 9 month old plant grown in the landscape. Color determinations were made in accordance with The 2007 Royal Horticultural Society Colour Chart from London England, except where general color terms of ordinary dictionary significance are used. Growing requirements are similar to the species.

Botanical classification: *Nemesia foetens* 'FLEURFRAM'.
Family:
Genus: *Nemesia.*
Species: *foetens.*
Denomination: 'FLEURFRAM'.
Common name: *Nemesia.*
Suggested uses: For use in the garden border, in patio containers or in the landscape.
Suggested commercial container size: 9 cm or 1-litre containers.
Cultural needs: Full sun, moist well-draining soil or peat-based medium, and application of a general plant fertilizer during the growing season.
Parentage:
*Female parent.*—*Nemesia* code number '832' (unpatented).
*Male parent.*—*Nemesia* code number '825' (unpatented).
Propagation: Softwood cuttings.
Growth habit: Upright, compact habit.
Vigor: Vigorous.
Plant dimensions: A 6 months old plant of 'FLEURFRAM' grown in a 9 cm. container is 15 cm. in height and 10-12 cm. in width. A 9 months old plant of 'FLEURFRAM' grown in a 13 cm container is 25-30 cm. in height and 25-30 cm. in width.
Type: Perennial in USDA zones 9 and warmer; annual in zones colder than zone 9.
Seasonal interest: Flowers that are a raspberry red in color fading to a lilac blue as they age. The flowers also exhibit a contrasting maroon palate or "eye".
Time to initiate roots: Approximately 14 days are needed to develop roots on initial cuttings.
Temperatures to initiate rooting: The air temperature that is recommended for rooting is 16° Centigrade and the soil temperature that is recommended for rooting is 24° Centigrade.
Crop time: Approximately 8 weeks are needed to produce a finished 9 cm. container plant from a rooted cutting.
Root system: Fine.
Hardiness: Hardy to minus 6° Centigrade.
Disease and pest susceptibility: 'FLEURFRAM' is susceptible to aphid-transmitted viruses and to whitefly.
Special or recommended growing requirements:
*Pruning.*—Pinch back the growing tips when potting into the final growing container.
*Soil.*—70% medium grade peat, 10% coarse peat and 20% 12 mm bark.
Stem:
*Stem shape.*—Quadrate.
*Stem length.*—12 cm. in length.
*Stem diameter.*—3 mm. in diameter.
*Stem surface.*—Glabrous.
*Stem color.*—138B.
*Pubescence.*—None observed.
*Stem texture.*—Soft and flexible.
*Internode length.*—3.5 cm. between nodes.
*Branching habit.*—Basal branching.
Foliage:
*Leaf arrangement.*—Opposite.
*Type.*—Evergreen.
*Leaf shape.*—Ovate.
*Leaf division.*—Simple.
*Apex.*—Acute.
*Base.*—Rounded.
*Margins.*—Entire.
*Surface.*—Glabrous.
*Leaf pubescence.*—None observed.
*Leaf appearance* (*abaxial and adaxial surfaces*).—Matte appearance.
*Leaf length.*—Individual leaves range from 1.50 cm. to 3 cm. in length.
*Leaf width.*—Individual leaves range from 4 mm. to 12 mm. in width.
*Leaf color* (*adaxial surface*).—138A.
*Leaf color* (*abaxial surface*).—138B.
*Leaf attachment.*—Petiolate and sessile are present on an individual plant.
*Petiole shape.*—Sulcate.
*Petiole surface.*—Glabrous.

*Petiole dimensions.*—4 mm. in length and less than 1.25 mm. in diameter.
*Petiole color.*—138B.
*Vein pattern.*—Pinnate with mid-vein depressed on adaxial surface and protruding on abaxial surface.
*Vein color* (*adaxial and abaxial surfaces*).—138C.

Flowers:
*Flowering season.*—Spring and summer and fall.
*Fragrance.*—None.
*Self-cleaning or persistent.*—Self-cleaning
*Inflorescence dimensions.*—4 cm. in length and 4 cm. in width.
*Type of inflorescence.*—Terminal racemes.
*Overall appearance.*—A fully developed inflorescence bears newly-opened raspberry-red flowers in combination with older flowers which have aged and faded to lilac-blue in color.
*Quantity of flowers.*—A range of 5-8 flowers per inflorescence.
*Lastingness of individual flower.*—An individual flower lasts 7-10 days.
*Peduncle dimensions.*—3 cm. in length and 1 mm. in diameter.
*Peduncle shape.*—Quadrate.
*Peduncle surface.*—Glabrous.
*Peduncle color.*—138B.
*Pedicel dimensions.*—9 mm. in length and less than 0.50 mm. in diameter.
*Pedicel shape.*—Closest to cylindrical with one longitudinal furrow.
*Pedicel surface.*—Glabrous.
*Pedicel color.*—138B.
*Bud shape.*—Oval.
*Bud color.*—59D.
*Bud dimensions.*—5 mm. in diameter and 5 mm. in length.
*Quantity of buds.*—A range of 3-4 individual buds are present on an individual inflorescence.
*Flower shape.*—Personate.
*Flower dimensions.*—14 mm-17 mm in height, 10-17 in width, 4-5 mm in depth.
*Flower color* (*overall appearance*).—Varies between 60B as flowers first open, to 75B as flowers age and remain on the plant.
*Corolla.*—Tube pouch and spur attached to base.
*Corolla tube dimensions.*—9 mm. in length and 2 mm. in diameter.
*Corolla tube color* (*inner and outer surfaces*).—155B.
*Pouch and spur.*—Described below as nectary throat and funnel.
*Petal color and dimensions* (*flower newly opened*).—Upper lip dimensions: 5 mm. in width and 5 mm in length. Upper lip color (adaxial surfaces): 60B. Upper lip color (abaxial surfaces): 70C. Lower lip dimensions: 1 cm in width and 5 mm in length. Lower lip color (adaxial surfaces): 60B. Lower lip color (abaxial surfaces): 70C.
*Petal color and dimensions* (*oldest flower remaining on plant*).—Upper lip dimensions: 1.7 cm in width and 1 cm in length. Upper lip color (adaxial surfaces): 75B. Upper lip color (abaxial surfaces): 75C. Lower lip dimensions: 1.5 cm in width and 1 cm in length. Lower lip color (adaxial surfaces):75B. Lower lip color (abaxial surfaces): 75C.
*Pollinator guide lines* (*upper lip*).—Approximately 15 parallel fine guide lines 3-4 mm in length, 71A in color.
*Margins, upper lip.*—Entire.
*Margins, lower lip.*—Entire.
*Number of lobes* (*upper lip*).—Four lobes in number.
*Fused or unfused* (*upper lip*).—Lobes basally fused.
*Lobe dimensions* (*upper lip*).—Each lobe is 5 mm in width and 6 mm in length.
*Petal apex, upper lip.*—Rounded.
*Petal apex, lower lip.*—Emarginate.
*Upper lip surfaces* (*adaxial and abaxial*).—Glabrous.
*Lower lip surfaces* (*adaxial and abaxial*).—Glabrous.
*Calyx dimensions.*—3 mm. in length and 4 mm. in width.
*Calyx shape.*—Stellate.
*Sepals.*—Five in number.
*Sepal surface.*—Pubescent.
*Sepal apex.*—Acute.
*Sepal shape.*—Lanceolate.
*Sepal dimensions.*—2 mm. in length and 1 mm. in width.
*Sepal margin.*—Entire.
*Sepals fused or unfused.*—Basally fused.
*Sepal color* (*adaxial surface*).—138A.
*Sepal color* (*abaxial surface*).—138A.
*Palate color.*—61A-61B.
*Palate dimensions.*—2 mm in length and 3 mm in width.
*Nectary* (*pouch and spur*).—
*Nectary guide.*—Two adjacent yellow stripes, each 1.5 mm in length, 1 mm in width; color: 13A.
*Nectary throat* (*appears as pouch externally*).—Diameter at base of flower, 4 mm; interior color 76D, exterior color 76C.
*Nectary funnel* (*appears as spur externally*).—4 mm in length, 0.05 mm in diameter; color: 69D (both surfaces).
*Nectary surface.*—Smooth, semi-glossy.

Reproductive organs:
*Stamens.*—Four in number.
*Color of stamens.*—155A.
*Stamen dimensions.*—1 mm. in length and less than 0.25 mm. in diameter.
*Anther color.*—163C.
*Pollen.*—Moderate, color: 163C.
*Anther dimensions.*—Less than 0.50 mm. in length and less than 0.50 mm. in width.
*Pistil.*—One, color: 144D, dimensions: 1 mm. in length and 0.25 mm. in diameter.
*Ovary dimensions.*—0.50 mm. in height and 0.50 mm. in diameter.
*Ovary shape.*—Globular.
*Ovary position.*—Superior.
*Ovary color.*—144D.

Seed:
*Quantity of seed.*—Average of 2 seeds per capsule.
*Seed shape.*—Flattened ellipsoid.
*Seed color.*—200D.
*Seed dimensions.*—2 mm. in length and 1.25 mm. in width.
*Capsule.*—Thin paper-like elliptic winged; dimensions 4 mm in length, 2.5 mm in width; color 156D.

I claim:

1. A new and distinct cultivar of *Nemesia* plant named 'FLEURFRAM' as described and illustrated herein.

* * * * *